United States Patent [19]

Bashkin et al.

[11] Patent Number: 4,857,167

[45] Date of Patent: Aug. 15, 1989

[54] OXYGEN-STABLE SUBSTITUTED FERROCENE REFERENCE ELECTRODE

[75] Inventors: James K. Bashkin, Clayton; Patrick J. Kinlen, High Ridge, both of Mo.

[73] Assignee: Monsanto Company, St. Louis, Mo.

[21] Appl. No.: 58,484

[22] Filed: Jun. 5, 1987

[51] Int. Cl.$^4$ .................. G01N 27/30; G01N 27/46
[52] U.S. Cl. .................................... 204/435; 556/143
[58] Field of Search ............... 204/1 E, 403; 435/817

[56] References Cited

U.S. PATENT DOCUMENTS

| 4,545,382 | 10/1985 | Higgins et al. | 204/403 |
| 4,711,245 | 12/1987 | Higgins et al. | 204/403 |

FOREIGN PATENT DOCUMENTS 0125137  11/1984  European Pat. Off. ............ 435/817

OTHER PUBLICATIONS

Gritzner et al., *Pure Appl. Chem.*, 54 (1982), pp. 1528–1532.
Peerce et al., *J. Electroanal. Chem.*, 108 (1980), pp. 121–125.
Blubaugh et al., *Anal. Lett.*, 19 (1986), pp. 1777–1784.
Haimerl et al., *Angew. Chem. Int. Ed. Engl.*, 25 (1986), pp. 180 & 181.

*Primary Examiner*—T. Tung
*Attorney, Agent, or Firm*—Linda L. Lewis; Charles E. Smith; Arnold H. Cole

[57] ABSTRACT

A solid state reference electrode stable in the presence of oxygen having an electrically conductive material in contact with substituted ferrocene/ferrocenium ions.

12 Claims, No Drawings

OXYGEN-STABLE SUBSTITUTED FERROCENE REFERENCE ELECTRODE

FIELD OF THE INVENTION

This invention relates to a solid state substituted ferrocene reference electrode and a method of preparing the electrode.

SUMMARY OF RELATED ART

Commonly used reference electrodes such as the saturated calomel electrode or the silver/silver chloride electrode utilize a liquid junction, which includes an electrode compartment containing an aqueous saturated potassium chloride internal filling solution. The filling reference solution functions to define the electrode potential. The filling solution contacts the solution being tested, forming a liquid junction, through a porous filter. At high pressures, the solution being tested may leak back into the reference electrode compartment, contaminating the internal reference solution. Although this problem may be eliminated by internal pressurization of the reference electrode, this significantly complicates electrode design and increases cost. Reference electrodes having an aqueous filling solution are also not suitable for measuring the pH in non-aqueous solvents because irreproducible liquid junction potentials may exist between the aqueous and non-aqueous phases, which produce erroneous pH readings. Additionally, contamination of the non-aqueous solvent by water and other ions associated with the reference electrode may occur through the porous filter, causing incorrect measurements.

An alternative to the liquid junction electrode is one based on an entirely solid state design. G. Gritzner and J. Kuta, *Pure Appl. Chem.* 54 (1982) 127, disclose a ferrocene/ferrocenium ion (Fc/Fc+) redox couple which is solvent independent. Ferrocene is dicyclopentadienyl iron (II) of the structure:

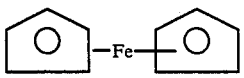

Ferrocene is oxidized to form the ferrocenium ion. Ferrocene/ferrocenium ions known in the art include ion salts, such as ferrocenium fluoroborate, ferrocenium perchlorate and ferrocenium hexafluorophosphate, monomers such as vinylferrocene, and polymers such as polyvinylferrocene. P. J. Peerce and A. J. Bard, *J. Electroanal. Chem.* 108 (1980) 121, disclose an electrode fabricated by coating polyvinylferrocene (PVFc) on platinum. The polymer coated electrode is brought to a 1:1 ratio of ferrocene to ferrocenium electrochemically by poising the electrode at the PVFc/Fc+ half-wave potential as determined by cyclic voltammetry. Although this electrode maintained constant reproducible potentials in deaerated acetonitrile, dissolution of the polymer in other aprotic solvents limited its use.

A. Haimerl and A. Merz, *Angew. Chem. Int. Ed. Engl.* attempted to fabricate reference electrodes by electrochemically copolymerizing ferrocene and pyrrole onto platinum. The electrodes were found to be stable for several hours in deaerated acetonitrile, but unstable in the presence of air.

M. Sato, T. Takeshi, and A. Nishimura, *Chem. Lett.* (1985) 925, have used cyclic voltammetry to show that dissolved ferrocenium ion rapidly decomposes in the presence of trace amounts of oxygen in DMSO. Thus, any electrochemically poised PVFc/Fc+ electrode exposed to air, would be expected to drift as Fc+ is consumed by oxygen. Successful utilization of such an electrode would require the elimination of exposure to air.

Higgins et al (U.S. Pat. No. 4,545,382) disclose a sensor electrode for in vivo use having an electrically conductive element coated with a combination of an enzyme and a mediator compound such as a polyhalogen, chloranil, ferrocene or a ferrocene derivative, such as dimethyl ferrocene. The mediator compound transfers electrons to the electrode when the enzyme is catalytically active. The dimethyl ferrocene electrode, however, is unstable in the presence of oxygen, and Higgins et al avoid oxidizing conditions when using the electrode.

We have discovered that sufficient substitution of the cyclopentadienyl rings of ferrocene prevents or retards the reaction of ferrocenium ion with oxygen. Such substituted ferrocenes are used to prepare reference electrodes which are stable in the presence of oxygen.

SUMMARY OF THE INVENTION

The present invention involves a solid state reference electrode and a method for making the electrode. The electrode comprises an electrically conductive material in contact with substituted ferrocene/ferrocenium ions wherein the cyclopentadienyl rings of the ferrocene and ferrocenium ions are sufficiently substituted to prevent or retard its reaction with oxygen.

The reference electrode is made by contacting an electrically conductive material with substituted ferrocene/ferrocenium ions wherein the substituted cyclopentadienyl rings of the ferrocene/ferrocenium ions are sufficiently substituted to prevent or retard their reaction with oxygen.

DETAILED DESCRIPTION OF THE INVENTION

The reference electrode of the present invention has an electrically conductive material in contact with substituted ferrocene/ferrocenium ions. The cyclopentadiene rings of the ferrocene and ferrocenium ions are sufficiently substituted to retard or prevent their reaction with oxygen.

As indicated hereinbefore, ferrocene and ferrocenium ions contain an iron atom or ion held covalently between two cyclopentadienyl rings. It is an electroactive organometallic compound, acting as a pH-independent reversible one-electron donor.

Suitable substituted ferrocenes which can be used in the present invention include octamethyl ferrocene, decamethyl ferrocene, octaphenylferrocene, octaethyl ferrocene, nonaethylferrocene, trimethylpentaethyl ferrocene, pentaphenylpentaethyl ferrocene and heptapropyl ferrocene. Substituted ferrocene monomers that can be polymerized to form substituted ferrocene polymers include octamethyldistyrylmethyl ferrocene, octamethyldivinyl ferrocene, octaethylvinyl ferrocene, triethylpentamethylvinylferrocene and octamethylvinylferrocene.

Ferrocenes which are not suitable for the electrodes of the present invention, because of their instability to oxygen include ferrocene, dimethyl ferrocene, vinyl ferrocene, divinyl ferrocene and the polymers thereof.

The substituted ferrocenium ions can be provided directly from the salt of the substituted ferrocenium ion. Suitable substituted ferrocenium salts include decamethylferrocenium hexafluorophosphate, decaethylferrocenium fluoroborate, decaphenylferrocenium perchlorate, octabutylferrocenium hexafluorophosphate and nonaethylferrocenium perchlorate.

A mixture of ferrocene and ferrocenium ions can be achieved using a single form of the ferrocene by electrochemically poising the ferrocene. This is accomplished by a method disclosed by R. N. Adams, "Electrochemistry of Solid Electrodes," Marcel Dekker, New York, N.Y. 1969, which is hereby incorporated by reference, to provide a mixture of ions. The method involves partially reducing the ferrocenium ion or partially oxidizing the ferrocene by holding the potential at the respective cyclic voltammetric peak until the current decayed to background levels. The mixture of ferrocene and ferrocenium ion can be in the range of 1/99 to 99/1 wt/wt ferrocene/ferrocenium. A preferred mixture is in the range of 40/60 wt/wt of ferrocene/ferrocenium ions to 60/40 wt/wt.

The term preventing or retarding the reaction with oxygen means that the rate of reaction is sufficiently slow that it is not detected by cyclic voltammetry or other methods. Cyclic voltammetry is described in detail in *Electrochemical Methods*, A. J. Bard and L. R. Faulkner, John Wiley and Sons, 1980, which is hereby incorporated by reference. Cyclic voltammetry varies the potential of an electrode linearly with time while measuring the current. The potential is moved in a positive direction until an oxidation current peak is detected and passed. The potential is reversed and moved in a negative direction past the reduction current peak until the original potential is reached. A plot voltammogram is a plot of current versus potential. When the substituted ferrocene/ferrocenium ions being measured are essentially infinite (as in a solution) the ratio of the peak of the reduction current to the peak of the oxidation current is about one (1.0). When the ferrocene/ferrocenium ions react with oxygen, the above ratio is less than about 0.90. Thus, a peak ratio in the range of about 1.0 to about 0.90, indicates that the reaction with oxygen has been prevented or retarded.

The reactivity of the substituted ferrocene and ferrocenium ions with oxygen is measured differently when the substituted ferrocene/ferrocenium ions are a fixed quantity such as from a polymer coated onto the electrode. If the peak current generated by cyclic voltammetry remains constant with repeated cycles, it indicates that the ferrocenium ion has not reacted with oxygen and the electrode is stable to oxygen.

Stability of the reference electrode to oxygen can also be determined by measuring the stability of the potential generated by the reference electrode upon exposure to oxygen. If the reference electrode is stable with time when exposed to oxygen, such that the potential does not drift appreciably, e.g., if the measured pH does not drift more that about 1 point in about twelve hours, the electrode is considered to be stable to oxygen.

The electrically conductive material of the electrode can be any material known in the art to be conductive, such as platinum, silver, conductive ceramics or carbon either as a pre-formed rod or as an electrode shape made up from a paste of carbon particles which contain the substituted ferrocene/ferrocenium ions. The surface of a solid electrode is such that the substituted ferrocene maintains contact with it. If metal, the surface is cleaned and roughened where it contacts the substituted ferrocene/ferrocenium ions. If solid carbon, the surface is "oxidized" i.e. heat-treated in an oven with oxygen access to provide an adhering surface.

The electrically conductive material can be a solid or a stiff paste of particles. The substituted ferrocene/ferrocenium ions may be contacted in a number of ways, for example:

(a) for a monomeric substituted ferrocene, by deposition from a solution in a readily evaporable liquid e.g. an organic solvent such as toluene;

(b) for a polymeric substituted ferrocene, deposition from a readily evaporable liquid, e.g., an organic solvent for the polymer such as chloroform;

(c) for a polymerisable substituted ferrocene monomer, by inducing polymerization in situ, e.g. by dissolving a substituted vinylferrocene in an organic solvent containing a free radical initiator and irradiating;

(d) by covalent modification of the carbon electrode e.g. by carbodiimide cross linking of the substituted ferrocene onto the carbon.

A paste can be prepared by mixing graphite, a conducting powder or polymer and oil such as Nujol or bromoform to form the paste. The substituted ferrocene/ferrocenium ions are mixed with the graphite paste. The concentration of the ferrocene/ferrocenium ions in the paste is in the range of 1 to 99 wt./wt. The preferred range is 10 to 90 wt/wt. The ratio of powder to oil in the paste is from 1:1 to 1:2 wt. to wt. ratio. The paste containing ions is contacted with the conducting material by packing it into a cup such as a piece of polytetrafluoroethylene tubing slipped over the end of a rod or disk of the conducting material.

The reference electrode of the present invention can be used in combination with an indicator electrode to form a pH meter.

The following examples are for illustrative purposes only and are not meant to limit the claimed invention in any manner.

EXAMPLES

The following reference electrodes were made according to the present invention:

Example 1

A substituted ferrocene/ferrocenium ion reference electrode using decamethyl ferrocene was constructed using a conductive graphite paste. The graphite paste was prepared using the method of R. N. Adams, "Electrochemistry at Solid Electrodes," Marcel Dekker, New York, 1969, pp. 280–283 which is hereby incorporated by reference. 1.0 gm of AGSX graphite powder purchased from Union Carbide was mixed with 0.84 gm of high purity mineral oil purchased from Aldrich to form the graphite paste. 0.1 gm decamethyl ferrocene and 0.1 gm decamethylferrocenium(III) hexafluorophosphate was then mixed with 0.8 gm of the graphite paste. This procedure loads the paste with equal weights of ferrocene/ferrocenium ion, and thereby poises the electrode potential. Alternatively, the graphite paste could be loaded with either the oxidized or reduced forms of the substituted ferrocene and the electrode potential electrochemically poised by partially reducing the ferrocenium or partially oxidizing the ferrocene ion by holding the potential at the cyclic voltammetric half wave potential until the current decayed to background levels.

Heat shrinkable Teflon polytetrefluoroethylene tubing was used to form a small cup at the end of a platinum disk electrode. The cup was packed with the graphite paste and smoothed using a small spatula.

The stability of the carbon paste decamethylferrocene/decamethyl ferrocenium electrode was then tested in air-saturated aqueous buffer systems. The potential of the electrode containing the substituted ferrocene was independent of pH (E=115 (+/−20) mV vs SCE), whereas the potential of the carbon paste electrode without ferrocene exhibited an irreproducible pH-potential response. The data are as follows:

| pH | Potential (mV) | |
|---|---|---|
| | Ferrocene Electrode | Carbon Electrode |
| 2.0 | 102, 108, 119 | −60, 30, 100, −140 |
| 4.0 | 135, 131 | |
| 7.0 | 105 | |
| 10.0 | 110, 119, 110–130 | 65, 87 |

A certain amount of scatter and drift is expected in potential data generated by electrodes, as can be seen by the data generated above. Scatter of +or −10 mV is considered within experimental limitations. A scatter of greater than 100 mV, however, indicates that the electrode potential is irreproducible.

The potential of the above electrode did not drift with time in the presence of oxygen, indicating that the reference electrode of the present invention exhibited stability in the presence of oxygen.

Control 1

A reference electrode of an unsubstituted ferrocene was prepared by coating polyvinylferrocene on platinum as described by P. J. Peerce and A. J. Bard, supra, which is hereby incorporated by reference. The electrode was prepared by electroplating poly(vinylferrocenium) perchlorate onto a platinum disk. The polymer coated electrode was brought to a 1:1 ratio of ferrocene/ferrocenium by electrochemically poising the electrode.

The unsubstituted polyvinylferrocene electrode was tested for stability in the presence of oxygen with a series of cyclic-voltammograms. The peak current generated in the presence of oxygen decreased with each cycle, demonstrating a rapid reaction of ferrocenium with oxygen.

Example 2

A reference electrode of the present invention using octamethyldistyrylmethyl ferrocene polymer as the substituted ferrocene/ferrocenium ion was prepared below. The octamethyldistyryl ferrocene monomer was prepared under an argon atmosphere as follows:

Tetramethylcyclopentadiene (5g), was added to 25ml dry, degassed THF. Butyl lithium (18ml of a 2.5M solution) was dissolved in 50ml toluene, and the solutions were combined. A white precipitate appeared, and the reaction became warm. The reaction mixture was refluxed for 1 hr, and the desired product, lithium tetramethylcyclopentadiene salt, a white solid, was collected by filtration. Dry petroleum ether was added to the solid, followed by 6.2g chloromethylstyrene. The reaction was refluxed overnight.

To the milk-white reaction mixture of lithium tetramethylcyclopentadiene salt, petroleum ether and chloromethylstyrene was added 4 ml 12-crown-5 ether, along with 100ml THF, and the reaction was refluxed 2 h. Butyl lithium (18 ml of a 2.5M solution) was added, turning the reaction mixture red and causing heat to be liberated. Ferrous chloride (5.2g) was then added to the reaction, and the reaction was refluxed for 3 days.

Flash chromatography on silica gel was performed after evaporating all solvent. A green material, determined by 1H NMR to be distyrylmethyl octamethyl ferrocene monomer, was eluted with slightly acidic alcohol, and was isolated as a hexafluorophosphate salt. The salt was purified twice by recrystallization, from acetone/ethanol and dichloromethane/diethylether.

The octamethyldistyrylmethyl ferrocene monomer was coated onto a glassy carbon electrode and polymerized to produce a reference electrode as follows:

A glassy carbon electrode was polished to clean the surface and placed in a beaker with the carbon surface pointed up. Approximately 10 mg solid distyrylmethyloctamethylferrocene monomer was placed on the surface, along with 2 mg $CHI_3$ which was used as a radical initiator. The mixture of solids was dissolved in 2 drops $CH_2Cl_2$, and the solution was dried by evaporation. This procedure was repeated 5 times. The electrode coated with monomer and $CHI_3$ was polymerized by photolyzing for 15 min. with a sun lamp giving a polymer film on the surface. Another few drops of $CH_2Cl_2$ were added, and some of the film dissolved, giving a green solution which indicated the presence of monomer. The solution film mixture on the electrode surface was photolyzed for 10 minutes more. The "dissolve/photolyze" procedure was repeated, until very little green color was observed which indicated almost complete polymerization. The electrode was left in the air to dry overnight.

The electrode was tested for stability in the presence of oxygen with a series of cyclic voltammograms. The peak current generated with each cycle was essentially unchanged, indicating stability in the presence of oxygen.

The following compounds were tested by cyclic voltammetry to determine their stability in the presence of oxygen. An electrolyte solution of the substituted ferrocene was prepared in acetonitrile (except decaphenyl ferrocene which was prepared in THF) with 0.1 molar of tetrabutylammonium fluoroborate and a cyclic voltammogram made. If the ratio of the peak of the reduction current to the peak of the oxidation current was less than 0.9, the substituted ferrocene was found to react with oxygen. The results are summarized below.

TABLE 1

| | Substituted Ferrocenium Ion | | |
|---|---|---|---|
| Source of Ferrocenium | (concentration, mmoles) | Peak Ratio | Stable Presence of Oxygen |
| dimethyl ferrocene | (8.2) | 0.80, 0.87 | No |
| octamethyl ferrocene | (10.0) | 0.97 | Yes |
| decamethyl ferrocene | (12.0) | 1.02 | Yes |
| decaphenyl ferrocene | (saturated soln. at STP) | 0.99 | Yes |

The results summarized in Table 1 indicate that octamethyl ferrocene, decamethyl ferrocene and decaphenyl ferrocene are suitable substituted ferrocene and ferrocenium ions for the electrodes of the present invention.

Example 3

A pH sensor was prepared by determining the electrical potential difference between the reference electrode of Example 1 and a glass electrode under the following pH conditions: A 0.1M phosphoric acid buffer solution was titrated with 1.0N sodium hydroxide from pH 1.5 to pH 12.5. The plot of pH versus potential difference generated by the pH sensor was essentially linear, indicating an effective pH sensor was prepared that could be used over a wide range of pH.

We claim:

1. A solid state reference electrode comprising an electronically conductive material in contact with substituted ferrocene/ferrocenium ion selected from the group consisting of octamethyl ferrocene, decamethyl ferrocene, octaphenyl ferrocene, octaethyl ferrocene, nonaethyl ferrocene, trimethyl pentaethyl ferrocene, pentaphenylpentaethyl ferrocene, heptapropyl ferrocene and polymers of octamethyl distyrylmethyl ferrocene, octamethyl vinyl ferrocene, octamethyldivinyl ferrocene, octaethylvinyl ferrocene and triethylpentamethylvinyl ferrocene.

2. The electrode of claim 1 wherein the conductive material is selected from the group consisting of silver, platinum and carbon.

3. The electrode of claim 1 wherein the conductive material is a carbon paste.

4. The electrode of claim 3 wherein the substituted ferrocene/ferrocenium ion is selected from the group consisting of octamethyl ferrocene, decamethyl ferrocene and octaphenyl ferrocene.

5. The electrode of claim 4 wherein the substituted ferrocene/ferrocenium ion is decamethyl ferrocene.

6. A pH sensor comprising the reference electrode of claim 1 in combination with an indicator electrode.

7. The pH sensor of claim 6 wherein the indicator electrode is a glass electrode.

8. A method for making a solid state reference electrode comprising contacting an electrically conductive material with substituted ferrocene/ferrocenium ions selected from the group consisting of octamethyl ferrocene, decamethyl ferrocene, octaphenyl ferrocene, octaethyl ferrocene, nonaethyl ferrocene, trimethyl pentaethyl ferrocene, pentaphenylpentaethyl ferrocene, heptapropyl ferrocene and polymers of octamethyl distyrylmethyl ferrocene, octamethyl vinyl ferrocene, octamethyldivinyl ferrocene, octaethylvinyl ferrocene and triethylpentamethylvinyl ferrocene.

9. The method of claim 8 wherein the conductive material is selected from the group consisting of silver, platinum and carbon.

10. The method of claim 8 wherein the conductive metal is a carbon paste.

11. The method of claim 10 wherein the substituted ferrocene/ferrocenium ion is selected from the group consisting of octamethyl ferrocene, decamethyl ferrocene and octaphenyl ferrocene.

12. The method of claim 8 wherein the ratio of the ferrocene and ferrocenium ion is poised electrochemically.

* * * * *